(12) United States Patent
Turcea et al.

(10) Patent No.: US 11,051,779 B2
(45) Date of Patent: Jul. 6, 2021

(54) PROCESSING IMAGE FRAMES OF A SEQUENCE OF CARDIAC IMAGES

(71) Applicant: Siemens Healthcare GmbH, Erlangen (DE)

(72) Inventors: Alexandru Turcea, Bușteni (RO); Costin Florian Ciusdel, Azuga (RO); Lucian Mihai Itu, Brasov (RO); Mehmet Akif Gulsun, Princeton, NJ (US); Tiziano Passerini, Plainsboro, NJ (US); Puneet Sharma, Princeton Junction, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 103 days.

(21) Appl. No.: 16/555,159

(22) Filed: Aug. 29, 2019

(65) Prior Publication Data
US 2020/0085394 A1 Mar. 19, 2020

(30) Foreign Application Priority Data
Sep. 13, 2018 (EP) .................... 18464002

(51) Int. Cl.
*G06T 7/00* (2017.01)
*G16H 30/40* (2018.01)
(Continued)

(52) U.S. Cl.
CPC ............ *A61B 6/504* (2013.01); *A61B 5/021* (2013.01); *A61B 5/0263* (2013.01); *A61B 5/352* (2021.01);
(Continued)

(58) Field of Classification Search
None
See application file for complete search history.

(56) References Cited

U.S. PATENT DOCUMENTS 9,595,089 B2 3/2017 Itu et al.
9,968,257 B1 * 5/2018 Burt ................ A61B 5/0035
(Continued)

FOREIGN PATENT DOCUMENTS

WO WO2012093266 A1 7/2012

OTHER PUBLICATIONS

Itu, L. M., et al. Personalized Blood Flow Computations: A Hierarchical Parameter Estimation Framework for Tuning Boundary Conditions, International Journal on Numerical Methods in Biomedical Engineering, vol. 33, Mar. 2017, pp. 1-21.
(Continued)

*Primary Examiner* — Idowu O Osifade

(57) ABSTRACT

A first sequence of cardiac image frames are received by a first neural network of the neural network system. The first neural network outputs a first set of feature values. The first set of feature values includes a plurality of data subsets, each corresponding to a respective image frame and relating to spatial features of the respective image frame. The first set of feature values are received at a second neural network of the neural network system. The second neural network outputs a second set of feature values relating to temporal features of the spatial features. Based on the second set of feature values, a cardiac phase value relating to a cardiac phase associated with a first image frame is determined.

20 Claims, 7 Drawing Sheets

(51) Int. Cl.
| | |
|---|---|
| *G06N 3/08* | (2006.01) |
| *A61B 6/00* | (2006.01) |
| *A61B 5/00* | (2006.01) |
| *A61B 5/021* | (2006.01) |
| *A61B 5/026* | (2006.01) |
| *A61B 5/352* | (2021.01) |

(52) U.S. Cl.
CPC .......... *A61B 5/7264* (2013.01); *A61B 5/7267* (2013.01); *A61B 6/485* (2013.01); *G06N 3/08* (2013.01); *G06T 7/0016* (2013.01); *G16H 30/40* (2018.01); *G06T 2207/10016* (2013.01); *G06T 2207/20081* (2013.01); *G06T 2207/30048* (2013.01)

(56) References Cited

U.S. PATENT DOCUMENTS

| | | | |
|---|---|---|---|
| 10,068,669 | B2 | 9/2018 | Mansi et al. |
| 2010/0310140 | A1* | 12/2010 | Schneider .................. G06T 7/35 382/130 |
| 2012/0041301 | A1 | 2/2012 | Redel |
| 2016/0106321 | A1* | 4/2016 | Sharma ..................... G06T 7/20 600/407 |
| 2016/0148372 | A1 | 5/2016 | Itu et al. |
| 2019/0025270 | A1 | 1/2019 | Tanaka et al. |
| 2020/0118266 | A1* | 4/2020 | Avendi ..................... G06T 7/162 |
| 2020/0193603 | A1* | 6/2020 | Golden ..................... G06T 7/11 |
| 2021/0000449 | A1* | 1/2021 | Deo ........................ A61B 8/485 |

OTHER PUBLICATIONS

Dutt, et al., Digital processing of ECG and PPG signals for study of arterial parameters for cardiovascular risk assessment, International Conference on Communications and Signal Processing (ICCSP), 2015.

Tröbs, M. et. al.: "Comparison of Fractional Flow Reserve Based on Computational Fluid Dynamics Modeling Using Coronary Angiographic Vessel Morphology Versus Invasively Measured Fractional Flow Reserve", in: The American Journal of Cardiology, 2016, vol. 117 (1), pp. 29-35.

Sethi, et al., Aortic stiffness: pathophysiology, clinical implications, and approach to treatment, Integr Blood Press Control. 2014; 7: 29-34.

Sen, et al.; Development and Validation of a New Adenosine-Independent Index of Stenosis Severity From Coronary Wave-Intensity Analysis Results of the ADVISE (ADenosine Vasodilator Independent Stenosis Evaluation) Study. J Am Coll Cardiol. 2012;59:1392-402.

Waechter, I. et al., Model-based blood flow quantification from rotational angiography, Medical Image Nalaysis, 2008, pp. 586-602.

Kong Bin et al: "Recognizing End-Diastole and End-Systole Frames via Deep Temporal Regression Network", Oct. 2, 2016 (Oct. 2, 2016), Image Analysis and Recognition : IITH International Conference, ICIAR 2014, Vilamoura, Portugal, Oct. 22-24, 2014, Proceedings, Part I; in: Lecture Notes in Computer Science, ISSN 1611-3349 ; vol. 8814.

Dezaki Fatemeh Taheri et al: "Deep Residual Recurrent Neural Networks for Characterisation of Cardiac Cycle Phase from Echocardiograms", Sep. 9, 2017 (Sep. 9, 2017), Image Analysis and Recognition : IIth International Conference, ICIAR 2014, Vilamoura, Portugal, Oct. 22-24, 2014, Proceedings, Part I; in: Lecture Notes in Computer Science, ISSN 1611-3349 ; vol. 8814.

Kaeppler, et al: "Motion Estimation Model for Cardiac and Respiratory Motion Compensation", Jun. 27, 2012 (Jun. 27, 2012), Information Processing in Computer-Assisted Interventions, Springer Berlin Heidelberg, Berlin, Heidelberg, pp. 94-103.

Bibicu, et al: "Cardiac Cycle Phase Estimation in 2-D Echocardiographic Images Using an Artificial Neural Network", IEEE Transactions on Biomedical Engineering, IEEE Service Center, Piscataway, NJ, USA, vol. 60, No. 5, May 1, 2013 (May 1, 2013), pp. 1273-1279.

Extended European Search Report (EESR) dated May 9, 2019 in corresponding European Patent Application No. 18464002.7.

* cited by examiner

PROCESSING IMAGE FRAMES OF A SEQUENCE OF CARDIAC IMAGES

RELATED CASE

This application claims the benefit of EP 18464002, filed on Sep. 13, 2018, which is hereby incorporated by reference in its entirety.

FIELD

The present embodiments relate to processing image frames of a sequence of cardiac images using a neural network.

BACKGROUND

For medical applications that involve imaging of the heart and vessels connected to the heart, there is often benefit in being able to determine the cardiac phase (i.e. the point in the cardiac cycle) at the time a given image frame is acquired. For example, there is often benefit in knowing whether an image frame was acquired during a systolic phase of the cardiac cycle or a diastolic phase of the cardiac cycle.

For example, coronary angiography is used in the assessment of Coronary Artery Disease and the anatomical severity of coronary stenosis is typically performed on end-diastolic angiographic image frames, when coronary artery motion is at a minimum. Some medical applications utilize a coronary stenosis diagnostic referred to as "instantaneous wave-free ratio" (iFR) that is used to assess whether a stenosis is causing a limitation of blood flow in coronary arteries (which can cause subsequent ischemia). iFR is measured with catheters (angiography) during a wave-free period of the diastolic phase of the cardiac cycle (i.e. a period during the diastolic phase in which the effect of pressure and/or velocity wave reflections from the distal or proximal portions of the vascular tree is minimal so that blood pressure may be assumed to vary linearly with blood flow rate).

Some medical applications utilize a reconstruction of a three-dimensional (3D) anatomical model of the heart and/or the coronary arteries. Such models are conventionally acquired using two coronary angiograms depicting arteries of interest. Since image quality is typically better during the mid to end portion of the diastolic phase of the cardiac cycle (i.e. when the heart itself is moving least), these images are usually selected for the reconstruction of an anatomical model.

In another example, measures of aortic stiffness, which is indicative of risk of heart disease and other ailments, are made by determining the percent diameter change of the ascending aorta from diastole to systole and multiplying the resulting value by the ratio of systolic and diastolic blood pressure.

Each of the above examples requires a determination of the cardiac phase associated with image frames of a set of images of the heart. Currently, to identify the cardiac phase associated with a given frame of a set of medical images, a medical professional will acquire a secondary dataset from which the cardiac phase can be determined and will correlate (in time) the respective cardiac phase with the frames of the set of medical images.

For example, in the example described above in which a reconstruction of a three-dimensional (3D) anatomical model of the heart is generated, electrocardiogram (ECG) measurements are acquired concurrent with the medical images, to allow identification of the cardiac phases (based on the ECG measurements) and subsequent association of a cardiac phase with a respective frame of a set of medical images.

Similarly, in the example described above in which an iFR value is to be measured, intravascular pressure measurements can be acquired concurrent with the medical images, which allow identification of the cardiac phase and therefore enable association of a cardiac phase with a respective frame of a set of medical images.

Similarly, in the determination of aortic stiffness, ECG measurements are acquired concurrent with the medical images to allow identification of the cardiac phases (based on the ECG measurements) and subsequent association of a cardiac phase with a respective frame of a set of medical images.

In each of the above-described examples, additional, sometimes invasive, medical steps or procedures are introduced to the clinical workflow in order to obtain information regarding cardiac phase associated with an image frame in a set of cardiac images. Such additional steps or procedures may introduce additional work (thereby reducing efficiency) and may introduce possible sources of error in the association between an image frame and the cardiac phase during which an image frame is acquired. Furthermore, in some circumstances, secondary data (such as ECG data) may not be available or low signal-to-noise ratio can make correlation between the image data and the secondary data, to correctly identify cardiac phases, difficult.

SUMMARY AND DESCRIPTION

These problems are solved or mitigated by the computer-implemented method embodiments, by the image processing apparatus embodiments, and by the computer program product embodiments.

The present embodiments relate in one aspect to a computer-implemented method of processing image frames of a sequence of cardiac images using a neural network. The method including: sequentially receiving a first sequence of image frames at a first neural network of the neural network system, the first sequence of image frames including a sequence of images of a cardiovascular system; outputting from the first neural network a first set of feature values, the first set of feature values including a plurality of data subsets, each corresponding to a respective image frame of the first sequence of image frames and relating to spatial features of the respective image frame; receiving the first set of feature values at a second neural network of the neural network system, different from the first neural network; outputting from the second neural network a second set of feature values relating to temporal features of the spatial features; and performing a determination process to determine, based on the second set of feature values, a cardiac phase value relating to a cardiac phase associated with a first image frame of the first sequence of image frames.

One embodiment relates in one aspect to a method wherein each of the plurality of data subsets include a feature vector relating to a respective image, and the method includes concatenating the data subsets to generate the first data set.

One embodiment relates in one aspect to a method wherein the first neural network includes a first convolutional neural network and the second neural network includes a second convolutional neural network.

One embodiment relates in one aspect to a method wherein the cardiac phase value includes a first probability value indicating a probability that the first image frame is associated with the cardiac phase.

One embodiment relates in one aspect to a method wherein the determination process includes receiving the second set of feature values at a third neural network of the neural network system and generating the probability value based on an output of the third neural network.

One embodiment relates in one aspect to a method including: receiving a second sequence of image frames at the first neural network, the second sequence of image frames overlapping with the first sequence of image frames such that the second sequence of image frames includes the first image frame and includes at least one further image frame not included in the first sequence of image frames; outputting from the first neural network a third set of feature values, the third set of feature values including a plurality of data subsets, each corresponding to a respective image frame of the second sequence of image frames and relating to spatial features of the respective image frame; receiving the third set of feature values at the second neural network; outputting from the second neural network a fourth set of feature values relating to temporal features of the spatial features of the respective image frame of the second sequence of image frames; and determining a second probability value indicating a probability that the first image frame is associated with the cardiac phase.

One embodiment relates in one aspect to a method including providing an output indicating a cardiac phase associated with first image frame based on the first probability value and the second probability value.

One embodiment relates in one aspect to a method including selecting one of the first probability value and the second probability value based on respective confidence values associated with the first probability value and the second probability value, and providing an output indicating a cardiac phase associated with first image frame based on the selected one of the first probability value and the second probability value.

One embodiment relates in one aspect to a method wherein the first sequence of image frames includes training data for training the neural network system, and the method includes performing a comparison process comparing the cardiac phase value with a ground truth value and performing a training process to train the neural network system on the basis of the comparison.

One embodiment relates in one aspect to a method including training the neural network system based on a loss function L:

a. $L = \begin{cases} y_{pred} - y_{GT}\ln(y_{pred}), & \text{when } y_{GT} \geq 0.5 \\ (1 - y_{pred}) - (1 - y_{GT})\ln(1 - y_{pred}), & \text{when } y_{GT} < 0.5 \end{cases}$ wherein $y_{pred}$ is the cardiac phase value and $y_{GT}$ is the ground truth value.

One embodiment relates in one aspect to a method including performing a generating process to generate the first sequence of image frames, the generating process including: generating a set of synthetic arterial trees; performing blood flow and contrast agent simulations in relation to the set of synthetic arterial trees for each of a plurality of different physiological and/or pathological conditions; projecting time-resolved results of the contrast agent propagation simulation into different planes to generate a plurality of synthetic angiograms; and generating ground truth values on the basis of the plurality of synthetic angiograms.

One embodiment relates in one aspect to a method wherein the cardiac phase associated with a first image frame includes one of a systolic cardiac phase and a diastolic cardiac phase.

The present embodiments relate in one aspect to an image processing apparatus including a neural network system, the neural network system including: a first neural network arranged to: receive a first sequence of image frames, the first sequence of image frames including a sequence of images of a cardiovascular system; and output from the first neural network a first set of feature values, the first set of feature values including a plurality of data subsets, each corresponding to a respective image frame of the first sequence of image frames and relating to spatial features of the respective image frame; and a second neural network arranged to: receive the first set of feature values and output a second set of feature values relating to temporal features of the spatial features; wherein the image processing apparatus is arranged to determine, based on the second set of feature values, a cardiac phase value relating to a cardiac phase associated with a first image frame of the first sequence of image frames.

The present embodiments relate in one aspect to a computer program stored as instructions in a computer readable storage medium, the computer program being loadable into a memory unit of a data processing system, including program code sections to make a data processing system execute the method according to an aspect when the computer program is executed in said data processing system.

The computer program product can be, for example, a computer program or include another element apart from the computer program. This other element can be hardware, for example a memory device, on which the computer program is stored, a hardware key for using the computer program and the like, and/or software, for example a documentation or a software key for using the computer program.

The image processing may be performed on any image but in certain examples may be performed on a medical image. For example, the image may be acquired by a medical imaging device selected from the group of an X-ray fluoroscopy device, a computed tomography device, a magnetic resonance imaging device, a molecular imaging device, a single photon emission compute tomography (SPECT)-device, a positron emission tomography (PET)-device and combinations thereof. The medical imaging device can be, for example, a combination of an imaging modality and a therapy modality, in particular a radiation therapy modality.

Reference is made to the fact that the described methods and the described image processing apparatus are merely preferred example embodiments and that the invention can be varied by a person skilled in the art, without departing from the scope of the invention provided it is specified by the claims.

BRIEF DESCRIPTION OF THE DRAWINGS

The embodiments are illustrated below with reference to the accompanying figures. The illustration in the figures is schematic and highly simplified and not necessarily to scale.

DETAILED DESCRIPTION

Figure 1:
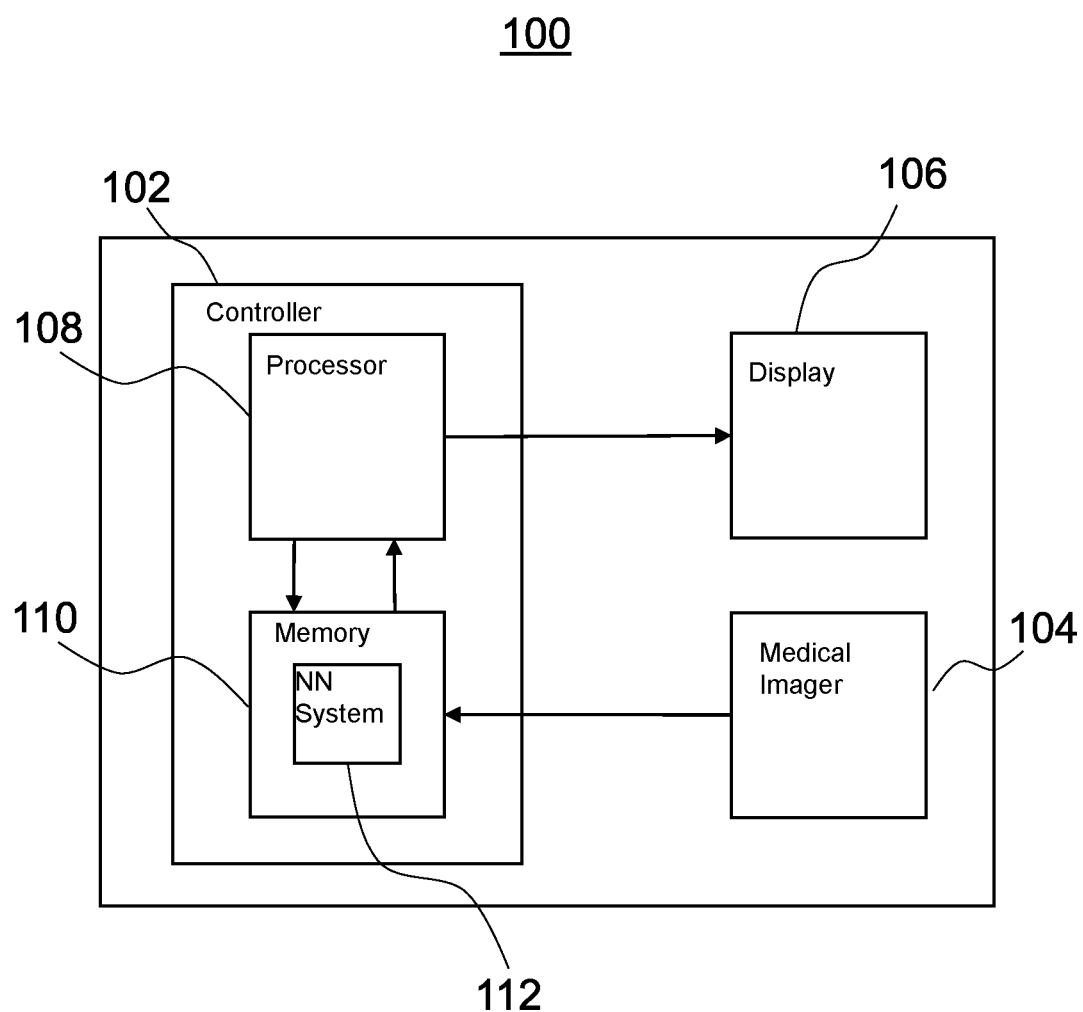
FIG. 1 is a schematic diagram of an image processing apparatus according to one embodiment.

FIG. 1 is a diagram illustrating an image processing apparatus 100 according to an embodiment. The image processing apparatus 100 includes a controller 102 for processing image data representative of frames of a medical image, according to the methods described herein. In some embodiments, the image processing apparatus 100 may include an medical imager 104 arranged to generate such image data. For example, the medical imager 104 may be an X-ray fluoroscopy unit arranged to generate X-ray fluoroscopy images and present them on a display 106.

The controller 102 may be arranged to generate display information relating to the images presented on the display 106.

The controller 102 may be implemented using hardware and/or software. In some examples, the controller 102 may include a processor 108 programmed to perform the functions of the controller 102.

The controller 102 may include a memory 110 arranged to store data in the form of a neural network system 112 implementing a plurality of neural networks that are trained by implementing a machine learning algorithm prior to installation and use of the image processing apparatus 100 in an operation setting. For example, the neural network system 112 may be trained by supplying training data to the neural network system 112 and the machine learning algorithm may learn to process image frames of a sequence of cardiac images using neural networks to determine a cardiac phase value relating to a cardiac phase associated with image frames of a sequence of image frames.

The machine learning algorithm may be any suitable algorithm implementing a neural network for processing image frames of a sequence of cardiac images to determine a cardiac phase value relating to a cardiac phase associated with image frames of a sequence of image frames. For example, the machine learning algorithm may include convolutional neural network (CNN) algorithms, which enable the neural network system 112 to be trained to determine a cardiac phase value relating to a cardiac phase associated with image frames of a sequence of image frames. In another example, the machine learning algorithm may be a fully convolutional neural network (FCN) algorithm. In another example, the machine learning algorithm may be a multi-layer perceptron (MLP) algorithm.

Furthermore, the memory 110 may store a computer program executable by the processor 108, to perform the methods described herein, and specifically the method described below with reference to FIG. 2.

The memory 110, may be any suitable form of memory. For example, the memory 110 may include volatile memory, such as random-access memory (RAM) and/or non-volatile memory such as read only memory (ROM) or flash memory. Furthermore, the memory 110 might include multiple, separate, memory devices and may include a combination of volatile and non-volatile memory. In some examples, certain component of the invention, such as the computer program and/or the model, may be stored in one memory device, while other components may be stored in another memory device. In other examples, the memory may be an associative memory.

Figure 2:
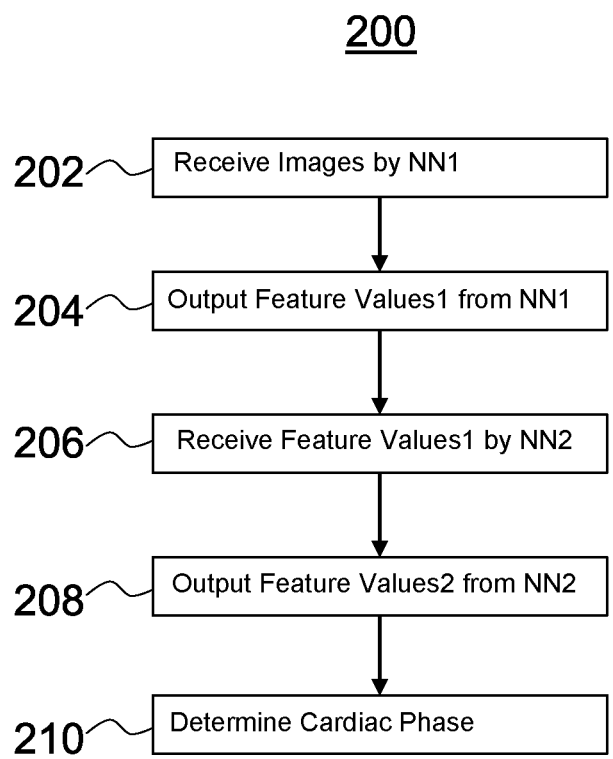
FIG. 2 is a simplified workflow diagram illustrating a computer-implemented method according to one embodiment.

FIG. 2 is a flow diagram depicting a method 200 of processing image frames of a sequence of cardiac images using a neural network system. For example, the method 200 may be implemented by the image processing apparatus 100 described above with reference to FIG. 1.

At block 202, a sequence of image frames is sequentially received at a first neural network of the neural network system, the sequence of image frames comprises a sequence of images of a cardiovascular system.

At block 204, a first set of feature values is output from the first neural network. The first set of feature values includes a plurality of data subsets, with each data subset corresponding to a respective image frame of the first sequence of image frames and relating to spatial features of the respective image frame. For example, the first neural network may be trained, as described below, to detect coronary arteries and to preselect a subset of frames in which coronary arteries are visible.

Coronary arteries display significant motion in an image sequence (such as a sequence of angiographic images) during a cardiac cycle. This motion is a compound effect of cardiac contraction, respiratory motion, and, in some cases, patient and/or table displacement. The neural network system 112 and the method 200 may be used to determine the cardiac phase of each image frame by implicitly analyzing these motion patterns.

At block 206, the first set of feature values is received at a second neural network of the neural network system, different from the first neural network.

At block 208, the second neural network outputs a second set of feature values relating to temporal features of the spatial features.

At block 210, a determination process is performed. The determination process determines, based on the second set of feature values, a cardiac phase value relating to a cardiac phase associated with an image frame of the sequence of image frames.

The method 200 may be used to enable, in a clinical setting for example, a determination of cardiac phases and/or time points of interest during the heart cycle using medical images (such as x-ray angiography, computed tomography, magnetic resonance imaging, ultrasound etc.) without the need for additional data from secondary measurements. In this case, the method 200 may be an "online" process (i.e. it is performed in an operational setting using real-time, previously unseen, image data).

The method 200 may also be used as part of a training process to train the neural network system 112, which may be performed prior to deployment of the image processing apparatus 100. The training process may be an "offline" process performed prior to deployment of an image processing apparatus 100 in an operational setting. During the training process a database of medical images and corresponding secondary data (e.g. ECG traces, arterial pressure plots etc.) is first assembled. Features of interest are extracted from the medical images and ground truth information regarding the cardiac phase and/or time points of interest of each heart cycle is determined from the corresponding secondary data. Using the features of interest and the ground truth information, the neural network system 112 learns a mapping between the features of interest in the medical images and the ground truth information. This mapping may then be used in an operational setting to process image frames of a sequence of cardiac images, as mentioned above.

In particular, in the training process, a first neural network of the neural network system 112 receives (sequentially) a sequence of image frames. The sequence of image frames received by the first neural network in the training phase includes a sequence of images of a cardiovascular system.

The first neural network outputs a first set of feature values (similar to the first set of features values described above with reference to FIG. 1), which is compared with ground truth data.

The ground truth data may be acquired by any appropriate manner. In some examples, the ground truth data may be acquired based on ECG measurements that can be correlated in time with the sequence of image frames.

Figure 3:
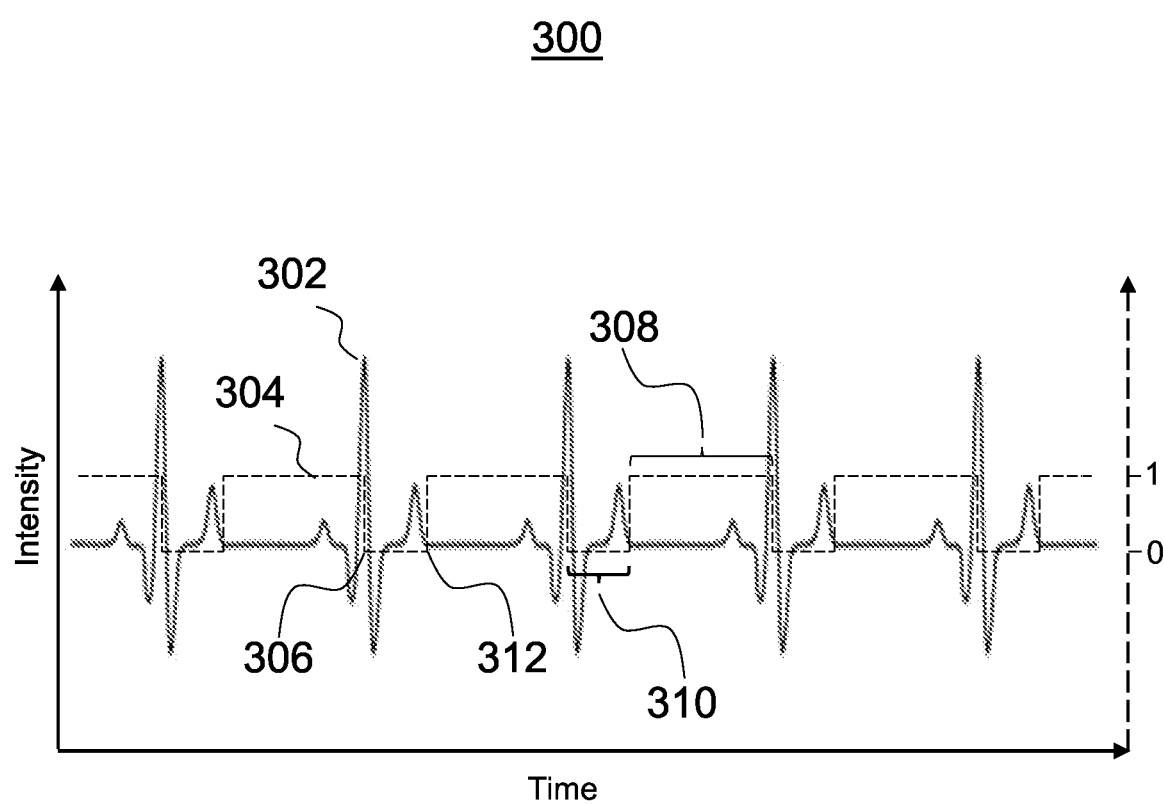
FIG. 3 is a schematic diagram of an example electrocardiogram overlaid with a trace identifying various cardiac phases.

FIG. 3 shows ECG data which may, in one example, be used to provide secondary data (i.e. ground truth information) for an image processing apparatus, such as the image processing apparatus 100 described above with reference to FIG. 1. FIG. 3 shows an ECG trace 302 (solid line) overlaid on which is plotted a ventricular systole-diastole plot 304 (dashed line) identifying the points in time when transitions between ventricular systole and ventricular diastole occur. In particular, at certain points in the systole-diastole plot 304, there are identified diastolic-to-systolic transitions 306 from a ventricular diastolic phase 308 to a ventricular diastolic phase 310. For example, diastolic-to-systolic transitions 306 may be identified by the R peaks of the QRS complexes shown in the ECG trace 302. At other points in the systole-diastole plot 304, there are identified systolic-to-diastolic transitions 312 from a ventricular systolic phase 310 to a ventricular diastolic phase 308. For example, systolic-to-diastolic transitions 312 may be identified by the ends of the T waves of the ECG trace 302 (e.g. by the time point corresponding to the first local minimum or maximum after the peak of the T wave. Accordingly, the corresponding cardiac phases (systole/diastole) may be mapped to each image frame.

In an operational setting, the frame which represents the end of the diastolic phase may be determined by identifying systolic and diastolic phases associated with frames of, for example, a sequence of angiographic images. The reason for this is that at this point in the cardiac phase the movement of the coronary arteries is at a minimum. Accordingly, as described above, this point is typically used, for example, for reconstructing a three-dimensional (3D) anatomical model of the heart and/or the coronary arteries and for determining measures relating to arterial stenosis. Accordingly, in some embodiments, the neural network system 500 (for example, the classifier 512) may be trained to identify the frame associated with the end of the diastolic phase (as identified by the diastolic-to-systolic transition 306 shown in FIG. 3).

Figure 4:
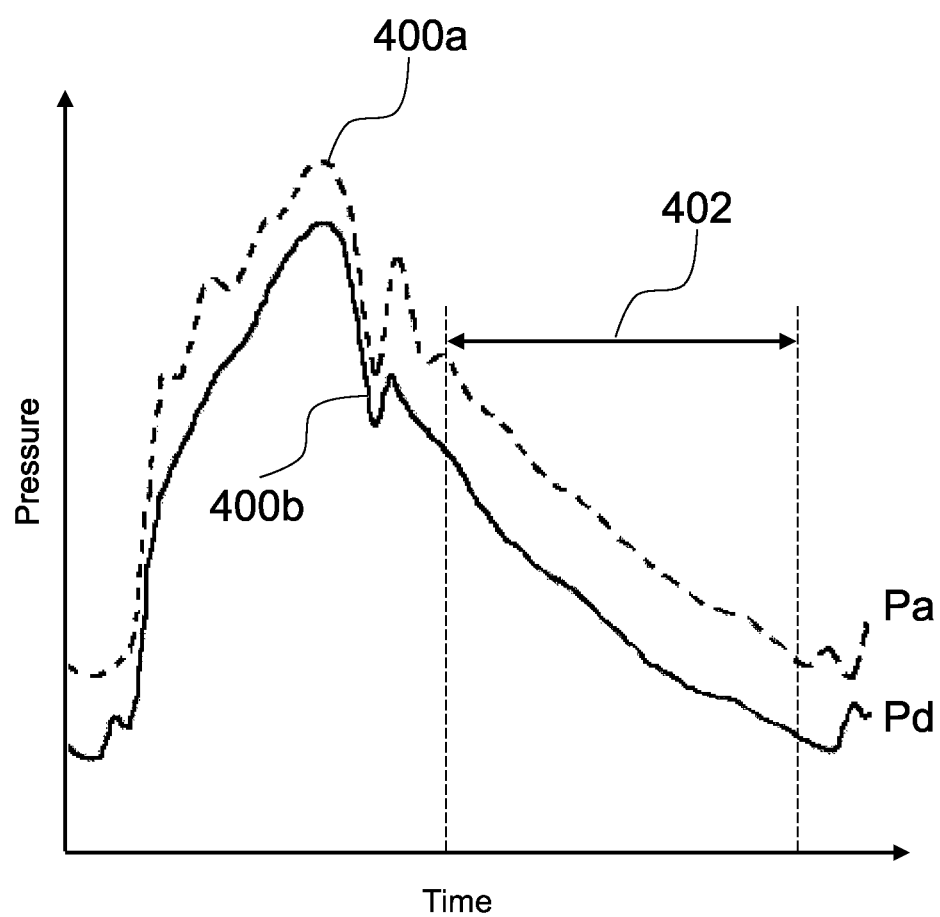
FIG. 4 is a schematic diagram of an example graph of intravascular pressure versus time, identifying a wave-free period.

FIG. 4 shows plots of intravascular pressure plotted against time which may, in another example, be used to provide secondary data (i.e. ground truth information) for an image processing apparatus, such as the image processing apparatus 100 described above with reference to FIG. 1. In particular, FIG. 4 shows a first plot 400a (dashed line), which is a plot of aortic blood pressure, Pa, which corresponds with the blood pressure measured at the ostium of the coronary vascular tree. FIG. 4 also shows a second plot 400b (solid line), which is a plot of so-called "distal" blood pressure, which is measured distally (with respect to the ostium) from one or multiple stenoses. The ratio of these two measurements is related to the degree of stenosis. In each of the plots 400a, 400b, a wave-free period 402 can be determined on the basis of the time-varying measurement of intravascular pressure.

In other embodiments, other measures relating to the cardiac cycle may be determined by the neural network system trained with appropriate training data. For example, the neural network system 112 may be trained to determine PR segment duration or ST segment duration. Furthermore, other cardiac phases such as atrial systolic and diastolic phases may be, alternatively or additionally, determined by the neural network system.

Training the neural network system to determine frames corresponding to the wave-free period may be important in applications which determine the instantaneous wave-free ratio (iFR) solely from medical images, as it may enable determination of the iFR without requiring any invasive pressure measurements. By correctly identifying the frames corresponding to the wave-free period, the contrast agent velocity, which provides a close approximation to the blood flow velocity during the wave-free period, may be determined.

Regardless of the imaging modality of the sequence of images or the nature of the secondary data (i.e. the form of the ground truth information), the neural network system 112 can learn a mapping between the features of interest in the medical images and the ground truth information provided by the secondary data.

Figure 5:
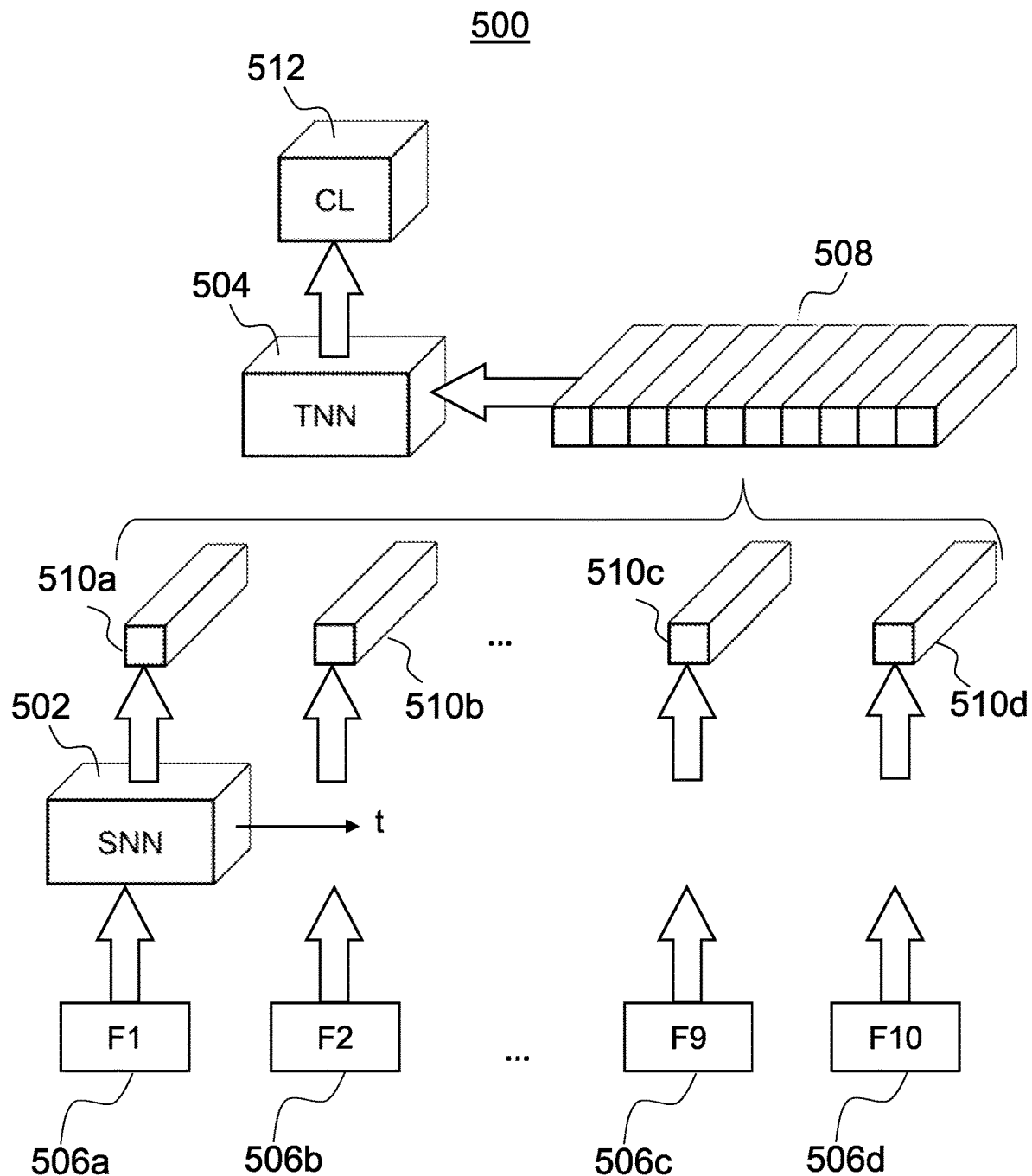
FIG. 5 is a schematic diagram of an example neural network algorithm for processing image frames of a sequence of cardiac images.

FIG. 5 shows a neural network system 500 configured to implement a method of processing image frames of a sequence of cardiac images, such as the method 200 described above with reference to FIG. 2. As explained above, the neural network system 500 may first be used in a training process (offline) and then may be used in an operational setting (online) to process image frames of a sequence of cardiac images.

In particular, the neural network system 500 shown in FIG. 5 includes a first neural network, referred to herein as a spatial neural network 502 (SNN) and a second neural network, referred to herein as a temporal neural network (TNN) 504.

The first neural network 502 is arranged sequentially to receive a first sequence of image frames 506a-506d (F1, F2 . . . F9 F10), the first sequence of image frames 506a-506d including a sequence of images of a cardiovascular system. The first neural network 502 is configured to output a first set of feature values 508 including a plurality of data subsets 510a-510d, each corresponding to a respective image frame 506 of the first sequence of image frames 506a-506d and relating to spatial features of the respective image frame. For example, the spatial features may relate to a location of a vessel border, a junction between vessels or a tip of a catheter inserted within a vessel. The values of the spatial features may, for example, be determined based on the image intensity of pixels or voxels in each image, and/or by the image intensity of neighbouring pixels or voxels.

In some applications, such as angiography, the image acquisition often starts before injecting a contrast agent and ends after the contrast agent has begun to be washed out by the coronary arterial blood flow. Therefore, in some embodiments, the frames of the sequence of cardiac images (e.g. coronary angiograms) may be filtered to extract only the frames that depict the coronary arteries (i.e. frames on which the contrast agent is present in the coronary arteries).

Any suitable approach may be used to perform such filtering. For example, in one embodiment, a neural network (such as a deep convolutional neural network), distinct from the first neural network, may be trained to perform a vessel segmentation task, i.e. the neural network is trained to detect pixels which represent coronary arteries.

The neural network performing the vessel segmentation task may produce, for each image frame, a probability map with the same size as the input image, where the value of each pixel represents the probability that the associated pixel from the input image is part of a coronary artery. A probability value indicating whether a given frame contains an image of a coronary artery may be determined, for example, as the pixel-wise sum of all probabilities for that frame and the neural network may select frames in which the sum of probability values meets or exceeds a threshold value.

Figure 6:
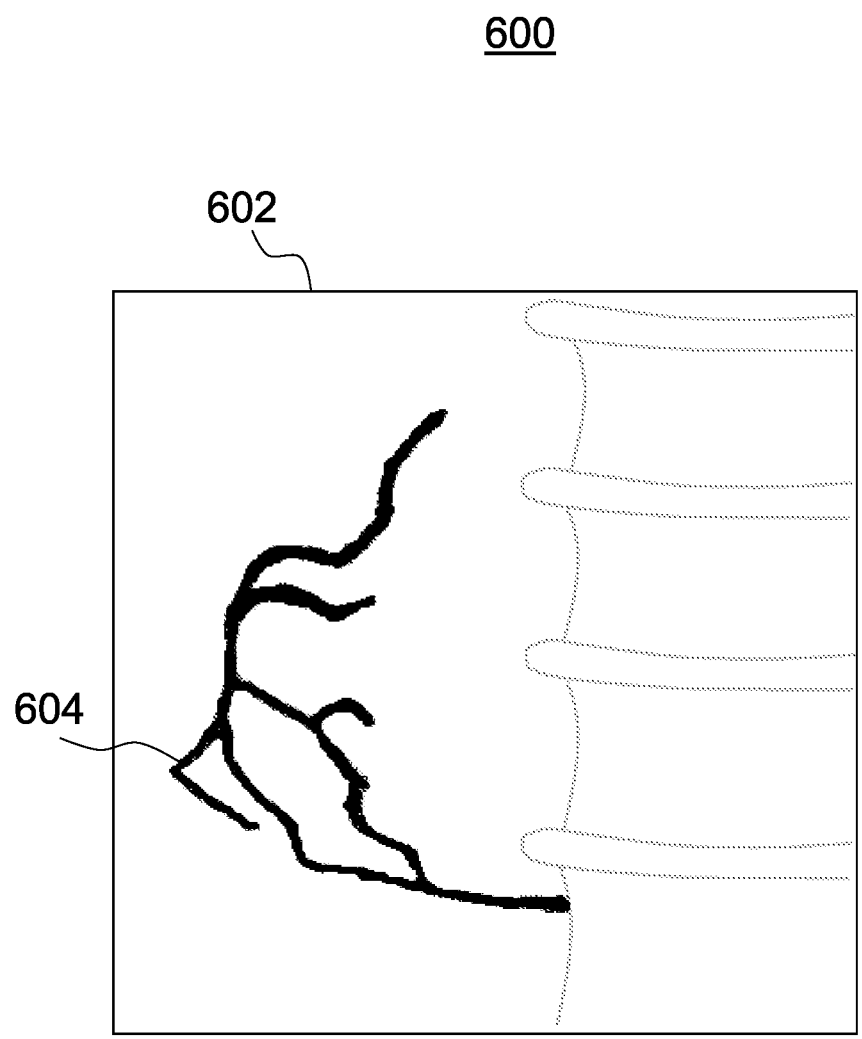
FIG. 6 is a schematic diagram illustrating an example probability map.

FIG. 6 shows an example of such a probability map 600, in which an image frame 602 is shown with an overlay 604 identifying regions of the image frame 602 likely to contain a coronary blood vessel (i.e. where contrast agent is present in the coronary arteries).

In some embodiments, the sequence of image frames (e.g. angiographic image frames) may be resampled at a rate of 10 fps in order to have a uniform and constant frame rate across the entire dataset. Accordingly, the first neural network 502 may take, as its input, a sequence of 10 frames (i.e. covering one second worth of acquired images).

The second neural network 504 is arranged to receive the first set of feature values 508 and output a second set of feature values (not shown in FIG. 5) relating to temporal features of the image frames.

Each of the data subsets 510a-510d may, for example, include a feature vector relating to a respective image. The datasets 510a-510d may be concatenated to form the first set of feature values 508, so that the first set of feature values 508 represents a time-ordered sequence representing variations in time of the spatial features of the cardio-vascular system. The first set of feature values 508 may be in the form of a feature value matrix, for example.

In some embodiments, the first neural network 502, the second neural network 504, or both neural networks 502, 504, may be a convolutional neural network.

The neural network system 500 also includes a classifier 512 (CL) arranged to perform a determination process. The determination process is based on the second set of feature values (received at the classifier 512) and determines a cardiac phase value relating to a cardiac phase associated with a first image frame of the first sequence of image frames 506a-506d.

In some embodiments, the classifier 512 may determine a cardiac phase value associated with each frame. For example, the cardiac phase value (associated with each frame) may be a probability that a respective image frame is associated with a particular cardiac phase (such as a systolic phase or a diastolic phase) or a transition between cardiac phases.

In some embodiments, the classifier 512 may be a third neural network (i.e. separate from the first and second neural network 502, 504); for example, the classifier 512 may be a convolutional neural network. The probability value may be based on the output of the third neural network.

The second set of feature values 508 may include a binary output, generating up to four probability values for the middle four frames in a ten-frame input sequence (with values between 0 and 1). During the training process, this binary output may be post-processed to optimize agreement with the ground truth information (i.e. provided by the secondary data).

Processing by the neural network system 500 may be achieved using a so-called "sliding window" over a larger sequence of cardiac image frames. For example, a second sequence of image frames may be received at the first neural network 502. The second sequence of image frames overlaps the first sequence of image frames such that the second sequence of image frames includes the first image frame and includes at least one further image frame not included in the first sequence of image frames.

The first neural network 502 may then output a third set of feature values including a plurality of data subsets, each of which corresponds to a respective frame of the second sequence of image frames and relates to spatial features of the respective image frame; i.e. similar in form to the first set of feature values but relating instead to the second sequence of image frames.

The third set of features values may then be received at the second neural network 504, which may output a fourth set of feature values relating to temporal features of the spatial features of the respective image frame of the second sequence of image frames; i.e. similar in form to the second set of feature values but relating instead to the second sequence of image frames.

The classifier 512 may then determine a second probability value indicating a probability that the first image frame is associated with the cardiac phase.

In some examples, the processes described above may be repeated using a sliding window of step-size one, for example, to produce two or more probability values for at least some frames (i.e. a first probability value and a second probability value). For example, in the example described above where second neural network 504 generates probability values for the middle four frames in a ten-frame input sequence, over the course of several steps, up to four probability values may be generated for some of the frames. In examples using a sliding-window, only frames having two or more associated probability values may be considered for determining the cardiac phase associated with a given frame. The probability value used for determining the cardiac phase associated with a given frame may be determined by aggregating the two or more probability values associated to each frame. The difference between each of the two or more probability values and the values representing the cardiac phases (e.g. the indices '0' or '1' described with reference to FIG. 3) is determined, which generates two or more confidence values for each frame. The probability value for a given frame that has the least difference (i.e. the highest confidence value) is determined to be the probability value having the highest confidence. Accordingly, it is that probability value that is used by the classifier 512 to determine the cardiac phase.

The classifier 512 provides an output indicating a cardiac phase associated with each image frame based on the probability value having the highest confidence value associated with that frame.

In an example embodiment, the neural network system 500 described above with reference to FIG. 5 may be trained in a training process and then used in an operational setting to process image frames of a sequence of cardiac images to determine systolic and/or diastolic cardiac phases based on angiographic medical images (e.g. X-ray angiography).

In the training process, secondary data may be provided, for example, by ECG data. The secondary data provides ground truth information. For example, referring to FIG. 3, a systolic phase of the cardiac cycle may be identified in the training process by portions of the ECG trace 302 with a binary value of 0, whereas a diastolic phase of the cardiac cycle may be identified in the training process by portions of the ECG trace 302 with a binary value of 1. For example, systolic phases (binary value 0) may be identified between the time point of an R peak and the time point corresponding to the first local minimum or maximum after the peak of the first T wave following the R peak. Similarly, diastolic phases (binary value 1) may be identified between the time point corresponding to the first local minimum or maximum after the peak of a T wave and the first R peak following the T peak. Such a binary signal may be associated with each frame in a sequence of image frames corresponding to a coronary angiogram, for example. However, in some embodiments, since some frames may represent a transition from systole to diastole, a floating-point value (i.e. a non-integer value between 0 and 1) may be associated with some frames of the sequence of image frames, with frames having such an associated floating-point value being considered transitionary frames.

During the training process, the sequence of image frames includes training data for training the neural network system 500. The neural network system 500 may perform a comparison process comparing the first probability value with a ground truth value and then perform the training process to train the neural network system 500 based on the comparison.

In some embodiments, during the training process, the neural network system 500 may use a loss function to train the first and second neural networks 502, 504 (and/or the classifier 512) in an end-to-end manner based on a Poisson distribution divergence. For example, the neural network system 500 may use a loss function, L:

$$L = \begin{cases} y_{pred} - y_{GT}\ln(y_{pred}), \text{ when } y_{GT} \geq 0.5 \\ (1 - y_{pred}) - (1 - y_{GT})\ln(1 - y_{pred}), \text{ when } y_{GT} < 0.5 \end{cases}$$

wherein $y_{pred}$ is the cardiac phase value and $y_{GT}$ is the ground truth value.

This function may more accurately determine a correct cardiac phase for a respective image frame as compared with other loss functions for frames associated with transitions between cardiac phases i.e. for which the ground truth values are non-integer values. This is because this loss function penalizes cases where the predicted cardiac phase is incorrect more than it penalises cases where there is a difference between the predicted phase and the ground truth value, but the predicted phase is nevertheless correct.

Although the training process described above utilizes a database of previously acquired medical images for the training process, in some embodiments, the neural network system 500 may be trained using synthetically generated image data.

For example, a dataset of synthetically generated image data may be generated by the following example method.

First a set of synthetic arterial trees is generated (as described in US patent application US20160148372). Using those synthetic arterial trees, blood flow and contrast agent propagation simulations may be performed under various conditions (as described by Itu, L. M., Sharma, P., Suciu, C., Moldoveanu, F., Comaniciu, D., in Personalized Blood Flow Computations: A Hierarchical Parameter Estimation Framework for Tuning Boundary Conditions, International Journal on Numerical Methods in Biomedical Engineering, Vol. 33, March 2017, pp. e028032017). This can be done, for example, by employing computational models describing full heart electromechanics to generate patterns of motion representative of a wide range of physiological and pathological conditions including: different heart rate values, different arterial wall stiffness values, different contrast agent injection rates profiles and/or volume profiles, different coronary physiological conditions (e.g. rest, hyperaemia, intermediate), and different aortic and/or venous pressures.

Synthetic coronary angiograms can then be generated by projecting time-resolved results of the contrast agent propagation simulation onto different planes characteristic for angiographic acquisitions (as described, for example, in US 20120041301).

Synthetic ground truth information, corresponding to the synthetic coronary angiograms, is then generated to be used to train the neural network system 500. For example, the electromechanical model described above may be arranged to produce corresponding ECG signals to be used as ground truth information for training the neural network system 500. Alternatively, temporal frames of the synthetically generated image data can be manually labelled with a label denoting a cardiac phase to which they correspond. For example, each synthetically generated frame may be labelled with a binary label identifying whether that frame is associated with a systolic or diastolic phase of the cardiac cycle, as described above with reference to FIG. 3.

Since the image data are synthetic, the ground truth information is precisely known.

Using synthetic image data rather than image data generated by acquiring images of real patients may be advantageous because a very large number of datasets can be generated in a relatively short time, thereby providing a more extensive database (i.e. containing a large range of cardiac cycles) with which to train the neural network system 500 at a reduced cost. Furthermore, generating synthetic image data enables image data representing images of complex or rare pathological configurations to be generated without the presence of a patient exhibiting those pathological conditions.

Figure 7:
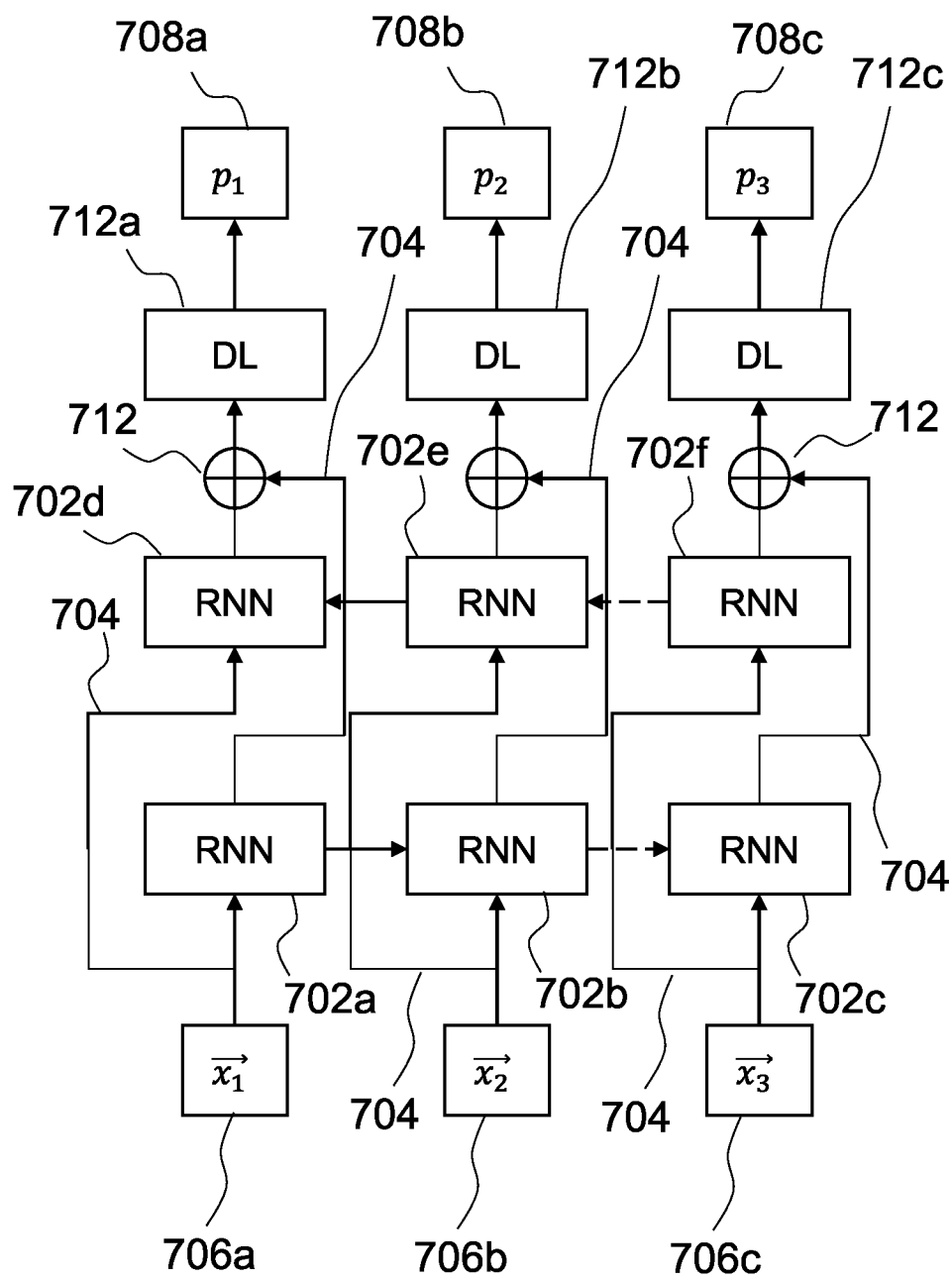
FIG. 7 is a schematic diagram of an example neural network algorithm for processing image frames of a sequence of cardiac images.

An alternative to the neural network system 500 described above with reference to FIG. 5 is the neural network system 700 shown in FIG. 7.

The neural network system shown in FIG. 7 uses a "Long Short-Term Memory" (LSTM) based approach to perform the classification of the frames. The neural network system 700 shown in FIG. 7 uses so-called "recurrent neural networks" that process a sequence of input events. Such recurrent neural networks each store an internal state that is updated based on the input events. The internal states of the recurrent neural networks determine an output relating to the cardiac phase of a respective image frame (e.g. whether that image frame is associated with a systolic cardiac phase or a diastolic cardiac phase). This enables the neural network system 700 to modulate its behaviour based on previous input events. LSTM (Long short-term memory) networks are a particular class of deep recurrent neural networks that perform well at learning phenomena that include a complex sequence of events. They combine the ability to recognize so-called "local" features of the sequence (i.e. "short-term" memory) together with the context (i.e. "long-term" memory) to which they are exposed. In the example cases described above, the neural network 700 is arranged to process an ordered sequence of cardiac image frames one-by-one (from the beginning to the end of the image acquisition), and to track how features represented in the sequence of image frames change from past frames to the current. This is enabled due to specialized neuron layers with dedicated internal state variables. The training process teaches the network how the internal state should be updated (i.e. how much information to keep or drop) every time a new frame is presented to the neural network system 700.

In particular, the architecture of the neural network system 700 shown in FIG. 7 includes stacked bidirectional recurrent neural network units (RNN) 702a-702f with skip connections 704 between all units in the stack. The neural network system 700 processes a sequence of features 706a-706c ($\vec{x}_1, \vec{x}_2, \vec{x}_3$), each extracted from one frame in the sequence of image frames; and returns for each frame of the sequence a probability value 708a-708c ($p_1, p_2, p_3$), which represents the probability that an image frame is associated with a particular cardiac phase (or e.g. a wave-free diastolic period or certain time points of interest during the cardiac phase such as peak systole, end systole, end diastole); for example the probability that an image frame is associated with a systolic phase of the cardiac cycle. The neural network system 700 processes the sequence of features 706a-706c in a forward direction starting with a first stack of RNNs 702a-702c and in backward direction with a second stack of RNNs 702d-702f. This allows the neural network system 700 to learn how the classification (i.e. the association with a particular cardiac phase) of a particular image frame relates to the classification of both previous and subsequent frames.

Each RNN 702a-702f includes multiple LSTM layers, so that each LSTM layer processes a sequence of hidden states provided by the previous layer (except the first LSTM layer, which processes the input features ($\vec{x}_1, \vec{x}_2, \vec{x}_3$)). Each probability value 708a-708c ($p_i$) is produced by concatenating the output of both stacks with a concatenation operator 710 and passing them to multiple shared dense layers 712a-712c (DL) with rectified linear unit ReLU activation, shrinking in size until there is only one linear output neuron in the layer.

In one embodiment, the neural network system 700 may replace the second neural network 504 (i.e. the temporal neural network) described with reference to FIG. 5. The neural network system 700 receives features 706 ($\vec{x}_1, \vec{x}_2, \vec{x}_3$) extracted from the original frame image using a spatial neural network such as the first neural network 502 described with reference to FIG. 5. A classifier, such as the classifier 512 described with reference to FIG. 5, is used to process the output of the RNNs 702a-702f (i.e. it replaces the dense layers 712a-712c shown in FIG. 7).

In some embodiments, the output of the neural network system 500, 700 may be used in a further process to provide diagnostic information. For example, the output of the neural network system 500, 700 may be received at a further neural network system which may be trained to detect rhythm abnormalities in the cardiac cycle based on, for example, determined cardiac phases signal. For example, large variations in various cardiac phases from normal cardiac cycles may indicate an abnormal cardiac rhythm. Additionally, or alternatively, other pathologies or cardiac abnormalities may also be determined by the further neural network. For example, these abnormalities may include one or more of:

Arrhythmias: supraventricular arrhythmias (such as sinus bradycardia, sinus tachycardia, sinus arrhythmia, non-sinus atrial rhythm, paroxysmal atrial tachycardia, atrial fibrillation, junctional rhythm), ventricular arrhythmias (such as premature ventricular contraction, idioventricular rhythm, ventricular tachycardia, ventricular fibrillation);

Abnormal activation sequence: atrioventricular conduction defects (such as first/second/third-degree atrioventricular block), bundle-branch block (such as left/right bundle-branch block), Wolff-Parkinson-White syndrome;

Abnormal wall thickness or size of the atria and/or ventricles: atrial enlargement (hypertrophy), ventricular enlargement (hypertrophy);

Myocardial ischemia and/or infarction: ischemia or infarction (e.g. based on abnormal ST segment elevation); and Abnormal electrolyte balance: e.g. potassium or calcium imbalances Carditis: e.g. pericarditis or myocarditis.

In some embodiments, additional neural networks may be employed to provide confidence and/or uncertainty values representing an estimation of confidence or uncertainty in the measures determined by the neural network systems described above. Such approaches may, for example, use synthetic data generated as described above to generate a large database of image data with which to train the respective neural network.

In embodiments such as biplane coronary angiography, where two or more image projections are acquired at the same time, both image sequences may be used as input data for the neural network system (e.g. using a multi-channel input) to improve the accuracy of the neural network system.

While the invention has been illustrated and described in detail with the help of a preferred embodiment, the invention is not limited to the disclosed examples. Other variations can be deducted by those skilled in the art without leaving the scope of protection of the claimed invention.

The invention claimed is:

1. A computer-implemented method of processing image frames of a sequence of cardiac images using a neural network system, the method comprising:
   sequentially receiving a first sequence of image frames at a first neural network of the neural network system, the first sequence of image frames comprising a sequence of images of a cardiovascular system;
   outputting from the first neural network a first set of feature values, the first set of feature values comprising a plurality of data subsets, each corresponding to a respective image frame of the first sequence of image frames and relating to spatial features of the respective image frame;
   receiving the first set of feature values at a second neural network of the neural network system, different from the first neural network;
   outputting from the second neural network a second set of feature values relating to temporal features of the spatial features; and
   determining, based on the second set of feature values, a cardiac phase value relating to a cardiac phase associated with a first image frame of the first sequence of image frames.

2. The computer-implemented method according to claim 1, wherein each of the plurality of data subsets comprises a feature vector relating to a respective image, and the method further comprising concatenating the data subsets to generate the first set of feature values.

3. The computer-implemented method according to claim 2, wherein the first neural network comprises a first convolutional neural network and the second neural network comprises a second convolutional neural network.

4. The computer-implemented method according to claim 1, wherein the cardiac phase value comprises a first probability value indicating a probability that the first image frame is associated with the cardiac phase.

5. The computer-implemented method according to claim 4, wherein determining comprises receiving the second set of feature values at a third neural network of the neural network system and generating the probability value based on an output of the third neural network.

6. The computer-implemented method according to claim 4, further comprising:
receiving a second sequence of image frames at the first neural network, the second sequence of image frames overlapping with the first sequence of image frames such that the second sequence of image frames includes the first image frame and includes at least one further image frame not included in the first sequence of image frames;
outputting from the first neural network a third set of feature values, the third set of feature values comprising a plurality of data subsets, each corresponding to a respective image frame of the second sequence of image frames and relating to spatial features of the respective image frame;
receiving the third set of feature values at the second neural network;
outputting from the second neural network a fourth set of feature values relating to temporal features of the spatial features of the respective image frame of the second sequence of image frames; and
determining a second probability value indicating a probability that the first image frame is associated with the cardiac phase.

7. The computer-implemented method according to claim 6, further comprising providing an output indicating a cardiac phase associated with first image frame based on the first probability value and the second probability value.

8. The computer-implemented method according to claim 7, further comprising selecting one of the first probability value and the second probability value based on respective confidence values associated with the first probability value and the second probability value, and providing an output indicating a cardiac phase associated with the first image frame based on the selected one of the first probability value and the second probability value.

9. The computer-implemented method according to claim 1, wherein the first sequence of image frames comprises training data for training the neural network system, and the method further comprises performing a comparison process comparing the cardiac phase value with a ground truth value and performing a training process to train the neural network system on the basis of the comparison.

10. The computer-implemented method according to claim 9, wherein performing the training comprises training the neural network system based on a loss function L:

$$L = \begin{cases} y_{pred} - y_{GT}\ln(y_{pred}), & \text{when } y_{GT} \geq 0.5 \\ (1 - y_{pred}) - (1 - y_{GT})\ln(1 - y_{pred}), & \text{when } y_{GT} < 0.5 \end{cases}$$

wherein $y_{pred}$ is the cardiac phase value and $y_{GT}$ is the ground truth value.

11. The computer-implemented method according to claim 9, further comprising generating the first sequence of image frames, the generating comprising:

generating a set of synthetic arterial trees;
performing blood flow and contrast agent simulations in relation to the set of synthetic arterial trees for each of a plurality of different physiological and/or pathological conditions;
projecting time-resolved results of the contrast agent propagation simulation into different planes to generate a plurality of synthetic angiograms; and
generating ground truth values on the basis of the plurality of synthetic angiograms.

12. The computer-implemented method according to claim 1, wherein the cardiac phase associated with a first image frame comprises one of a systolic cardiac phase and a diastolic cardiac phase.

13. The computer-implemented method according to claim 1, further comprising determining a transition between cardiac phases.

14. An image processing apparatus comprising a neural network system, the neural network system comprising:
a first neural network arranged to:
receive a first sequence of image frames, the first sequence of image frames comprising a sequence of images of a cardiovascular system; and
output from the first neural network a first set of feature values, the first set of feature values comprising a plurality of data subsets, each corresponding to a respective image frame of the first sequence of image frames and relating to spatial features of the respective image frame; and
a second neural network arranged to:
receive the first set of feature values and output a second set of feature values relating to temporal features of the spatial features;
wherein the image processing apparatus is arranged to determine, based on the second set of feature values, a cardiac phase value relating to a cardiac phase associated with a first image frame of the first sequence of image frames.

15. A non-transitory computer-readable storage medium comprising a computer program, the computer program being loadable into a memory unit of a data processing system, including program code sections executable by a data processing system, the program code sections comprising instructions to:
sequentially receive a first sequence of image frames at a first neural network of the neural network system, the first sequence of image frames comprising a sequence of images of a cardiovascular system;
output from the first neural network a first set of feature values, the first set of feature values comprising a plurality of data subsets, each corresponding to a respective image frame of the first sequence of image frames and relating to spatial features of the respective image frame;
receive the first set of feature values at a second neural network of the neural network system, different from the first neural network;
output from the second neural network a second set of feature values relating to temporal features of the spatial features; and
determine, based on the second set of feature values, a cardiac phase value relating to a cardiac phase associated with a first image frame of the first sequence of image frames.

16. The non-transitory computer-readable storage medium according to claim 15, wherein each of the plurality of data subsets comprises a feature vector relating to a respective image, and the instruction further comprising an instruction to concatenate the data subsets to generate the first set of feature values.

17. The non-transitory computer-readable storage medium according to claim 16, wherein the first neural network comprises a first convolutional neural network and the second neural network comprises a second convolutional neural network.

18. The non-transitory computer-readable storage medium according to claim 15, wherein the cardiac phase value comprises a first probability value indicating a probability that the first image frame is associated with the cardiac phase.

19. The non-transitory computer-readable storage medium according to claim 18, wherein determining comprises receiving the second set of feature values at a third neural network of the neural network system and generating the probability value based on an output of the third neural network.

20. The non-transitory computer-readable storage medium according to claim 18, the program code sections further comprising instructions to:

receiving a second sequence of image frames at the first neural network, the second sequence of image frames overlapping with the first sequence of image frames such that the second sequence of image frames includes the first image frame and includes at least one further image frame not included in the first sequence of image frames;

outputting from the first neural network a third set of feature values, the third set of feature values comprising a plurality of data subsets, each corresponding to a respective image frame of the second sequence of image frames and relating to spatial features of the respective image frame;

receiving the third set of feature values at the second neural network;

outputting from the second neural network a fourth set of feature values relating to temporal features of the spatial features of the respective image frame of the second sequence of image frames; and determining a second probability value indicating a probability that the first image frame is associated with the cardiac phase.

* * * * *